United States Patent
Reddy et al.

(10) Patent No.: US 10,226,618 B2
(45) Date of Patent: Mar. 12, 2019

(54) FIXATION DEVICE FOR A SUBCUTANEOUS ELECTRODE

(71) Applicant: CARDIAC PACEMAKERS, INC., St. Paul, MN (US)

(72) Inventors: G. Shantanu Reddy, Minneapolis, MN (US); Andrew L. De Kock, Andover, MN (US); Christopher Alan Fuhs, Roseville, MN (US); Jay Overcash, Wyndmoor, PA (US); Garth Mindermann, Bloomington, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/285,519

(22) Filed: Oct. 5, 2016

(65) Prior Publication Data

US 2017/0095657 A1   Apr. 6, 2017

Related U.S. Application Data

(60) Provisional application No. 62/237,755, filed on Oct. 6, 2015.

(51) Int. Cl.
*A61N 1/00* (2006.01)
*A61N 1/05* (2006.01)

(52) U.S. Cl.
CPC .................. *A61N 1/0504* (2013.01)

(58) Field of Classification Search
USPC ................................ 607/116, 126
See application file for complete search history.

(56) References Cited

U.S. PATENT DOCUMENTS

| | | | |
|---|---|---|---|
| 4,796,643 A | 1/1989 | Nakazawa et al. | |
| 5,713,945 A | 2/1998 | Fischer et al. | |
| 5,931,862 A | 8/1999 | Carson | |
| 7,493,175 B2 | 2/2009 | Cates et al. | |
| 7,655,014 B2 | 2/2010 | Ko et al. | |
| 8,086,324 B1 | 12/2011 | Vase | |
| 8,160,722 B2 | 4/2012 | Rutten et al. | |
| 8,483,841 B2 | 7/2013 | Sanghera et al. | |
| 2004/0102804 A1 | 5/2004 | Chin | |
| 2006/0122676 A1 | 6/2006 | Ko et al. | |
| 2006/0247753 A1* | 11/2006 | Wenger ............. | A61B 18/1492 607/126 |

(Continued)

FOREIGN PATENT DOCUMENTS

EP    0813885 A2   12/1997

OTHER PUBLICATIONS

International Search Report and Written Opinion, PCT/US/2016/055418, dated Dec. 14, 2016.

*Primary Examiner* — Nicole F Johnson
(74) *Attorney, Agent, or Firm* — Seager, Tufte & Wickhem LLP

(57) ABSTRACT

An illustrative anchoring mechanism is provided for attachment to an implantable subcutaneous lead to facilitate anchoring at the distal tip of the lead. The anchoring mechanism is attached to an opening in a distal portion of a subcutaneous lead prior to implantation. The anchoring mechanism may be designed to avoid covering the sensing electrode of the subcutaneous lead, to prevent interference with sensing. Use of such an apparatus may reduce the number of incisions needed to perform implantation.

19 Claims, 14 Drawing Sheets

(56) References Cited

U.S. PATENT DOCUMENTS

| | | |
|---|---|---|
| 2006/0287666 A1 | 12/2006 | Saadat et al. |
| 2008/0208247 A1 | 8/2008 | Rutten et al. |
| 2010/0030311 A1 | 2/2010 | Lazeroms et al. |
| 2010/0152798 A1 | 6/2010 | Sanghera et al. |
| 2012/0029335 A1 | 2/2012 | Sudam et al. |
| 2013/0131723 A1 | 5/2013 | Snell et al. |
| 2013/0267837 A1 | 10/2013 | Schulte et al. |
| 2013/0274845 A1 | 10/2013 | Kokones et al. |
| 2014/0350653 A1 | 11/2014 | Shiroff et al. |

* cited by examiner

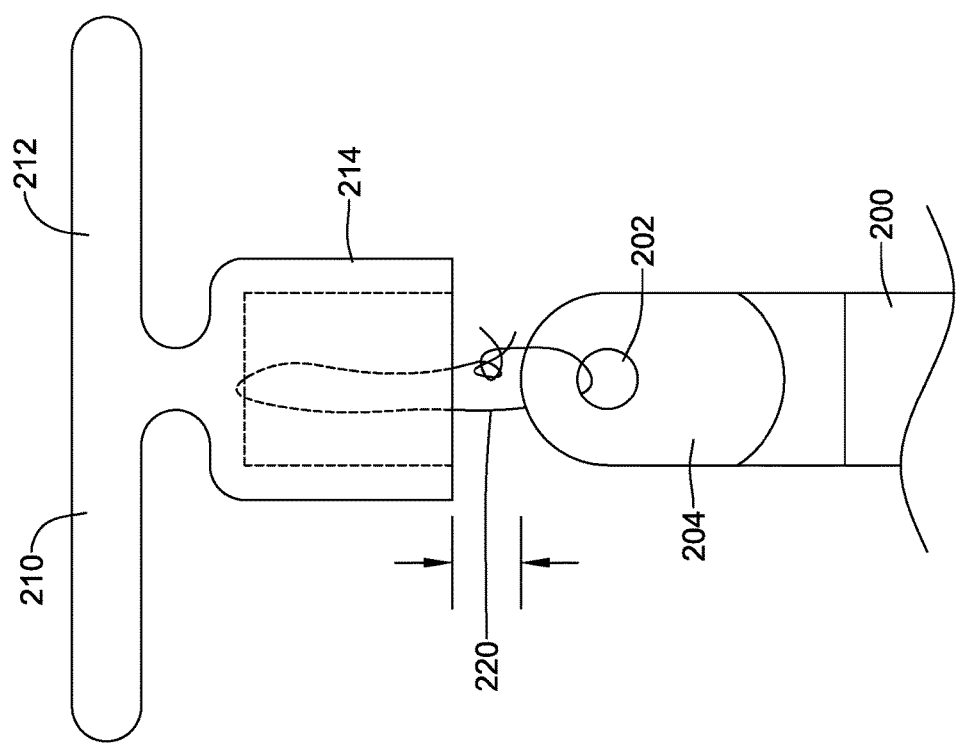

FIXATION DEVICE FOR A SUBCUTANEOUS ELECTRODE

CROSS REFERENCE TO RELATED APPLICATIONS

The present application claims the benefit of and priority to U.S. Provisional Patent Application Ser. No. 62/237,755, filed Oct. 6, 2015, titled FIXATION DEVICE FOR A SUBCUTANEOUS ELECTRODE, the disclosure of which is incorporated herein by reference.

BACKGROUND

The S-ICD System™ from Cameron Health, Inc., and Boston Scientific Corporation presents a new opportunity in cardiac rhythm management to reduce the complications associated with transvenous defibrillator systems. The defibrillator system itself may be implanted subcutaneously without accessing the vasculature or touching the heart.

An illustration is provided in FIG. 1. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may further include such components as would be appropriate for communication (such as RF communication, inductive telemetry or other suitable communication linkage) with an external device such as a programmer 22. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

As shown in FIG. 2, a typical implant for the S-ICD System uses three incisions 30, 32, 34, and a sterile field represented by shape 36 is used to avoid the introduction of microorganisms that can cause infection. Some physicians have also used a two-incision approach by foregoing the superior sternal incision 34.

The subcutaneous-only placement prevents some of the more dangerous complications associated with infection, in particular, endocarditis which can result when an infection travels down a transvenous lead into the heart. However, infections, both systemic and superficial have been reported. In addition, some reports have shown that air pockets at either of incisions 32 or 34 can lead to inappropriate shocks within the first few weeks of implantation.

Alternatives and additional options are desired to reduce the number of incisions.

OVERVIEW

The present inventors have recognized, among other things, that a problem to be solved is the anchoring of a subcutaneous lead. An anchoring device is provided for attachment to the implantable subcutaneous lead to facilitate anchoring at the distal tip of the lead. In some examples, the anchoring mechanism is attached at an opening in the distal end of a subcutaneous lead prior to implantation. The anchoring mechanism may be designed to avoid covering the sensing electrode of the subcutaneous lead, to prevent interference with sensing.

In a first illustrative embodiment, an anchoring device for use with a subcutaneous lead may comprise one or more arms, a body coupling the one or more arms together and having a nose on one end thereof, and an attachment feature for attaching to a distal tip of the subcutaneous lead.

Additionally, or alternatively, in some embodiments according to the first illustrative embodiment, the attachment feature may comprise a post extending in a lateral direction relative to a direction from the attachment feature to the nose, such that the post is configured to place through an opening in the tip of the subcutaneous lead.

Additionally, or alternatively, in some embodiments according to the first illustrative embodiment, a securing piece for securing to the post, wherein the securing piece and the post snap fit together.

Additionally, or alternatively, in some embodiments according to the first illustrative embodiment, the securing piece, attachment feature and body may be configured to mate together with the distal tip of the subcutaneous lead to form a smooth transition therebetween.

Additionally, or alternatively, in some embodiments according to the first illustrative embodiment, the post may include an expanded portion at a tip therefor, the expanded portion configured to pass through an opening, such as a suture hole of the subcutaneous lead in a snap-through fashion and remain secured to the subcutaneous lead after passing through the opening.

Additionally, or alternatively, in some embodiments according to the first illustrative embodiment, the attachment feature may comprise a hook for passing into an opening, such as a suture hole in the tip of the subcutaneous lead.

Additionally, or alternatively, in some embodiments according to the first illustrative embodiment, the attachment feature may further include a latch to allow entry of the subcutaneous lead an opening, such as suture hole, to the hook, but preventing escape therefrom.

Additionally, or alternatively, in some embodiments according to the first illustrative embodiment, the body may comprise a bore having a closed end near the nose and an open end for receiving a portion of the distal tip of the subcutaneous lead, and the attachment feature is a suture secured to the body within the bore.

Additionally, or alternatively, in some embodiments according to the first illustrative embodiment, the suture may be long enough to allow the lead to be outside the bore while remaining attached to the suture.

Additionally, or alternatively, in some embodiments according to the first illustrative embodiment, the attachment feature may be a tab having an opening, such as a suture hole therethrough to allow a suture or surgical staple to be used to secure the tab to the opening of the subcutaneous lead.

Additionally, or alternatively, in some embodiments according to the first illustrative embodiment, the arms, body and attachment feature may be formed of a single piece.

Additionally, or alternatively, in some embodiments according to the first illustrative embodiment, a dissolvable portion that may act as a filler during introduction of the anchoring device and an associated subcutaneous lead into a patient, and then, once dissolved by tissue fluids after implantation, to create a space between the body and the anchored subcutaneous lead.

Additionally, or alternatively, in some embodiments according to the first illustrative embodiment, the arms may be flexible and configured to collapse for introduction through an introducer sheath.

Additionally, or alternatively, in some embodiments according to the first illustrative embodiment, the arms may include a radiopaque coating thereon.

Additionally, or alternatively, in some embodiments according to the first illustrative embodiment, the device may further comprise one or more radiopaque strands or filaments therein.

In a second illustrative embodiment, a method of implanting a subcutaneous lead having a plurality of electrodes thereon and a distal tip having an opening, such as a suture hole may comprise securing an anchoring device to the distal tip using the opening prior to implanting the lead and advancing the lead, with the anchoring device secured thereto, through a subcutaneous tunnel to a desired implant location.

Additionally, or alternatively, in some embodiments according to the second illustrative embodiment, the method may further comprise using an introducer tool having a sheath thereon for creating the subcutaneous tunnel and removing the introducer tool to leave the sheath in place, wherein the step of advancing the lead, with the anchoring device secured thereto, is performed by advancing the lead and anchoring device through the sheath.

Additionally, or alternatively, in some embodiments according to the second illustrative embodiment, the anchoring device may comprise one or more arms thereon for anchoring in subcutaneous tissue, the one or more arms are flexible, the step of advancing the lead and anchoring device through the sheath is performed with the arms in a collapsed configuration, and upon completion of the step of advancing the lead and anchoring device through the sheath, the sheath is removed, allowing the arms to return from the collapsed configuration to an extended configuration for anchoring within the subcutaneous tissue.

Additionally, or alternatively, in some embodiments according to the second illustrative embodiment, the anchoring device may comprise one or more arms, a body coupling the one or more arms together and having a nose on one end thereof, and an attachment feature for attaching to a distal tip of the subcutaneous lead.

In a third illustrative embodiment an anchoring device for use with a subcutaneous lead may comprise one or more flexible arms, a body coupling the one or more arms together and having a nose on one end thereof, and an attachment feature for attaching to a distal tip of the subcutaneous lead, wherein the attachment feature is a snap-fit, a suture, or a hook.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8 shows a second anchoring device relative to the distal tip of a lead using a suture for attachment to the lead;

DETAILED DESCRIPTION

Figure 1:
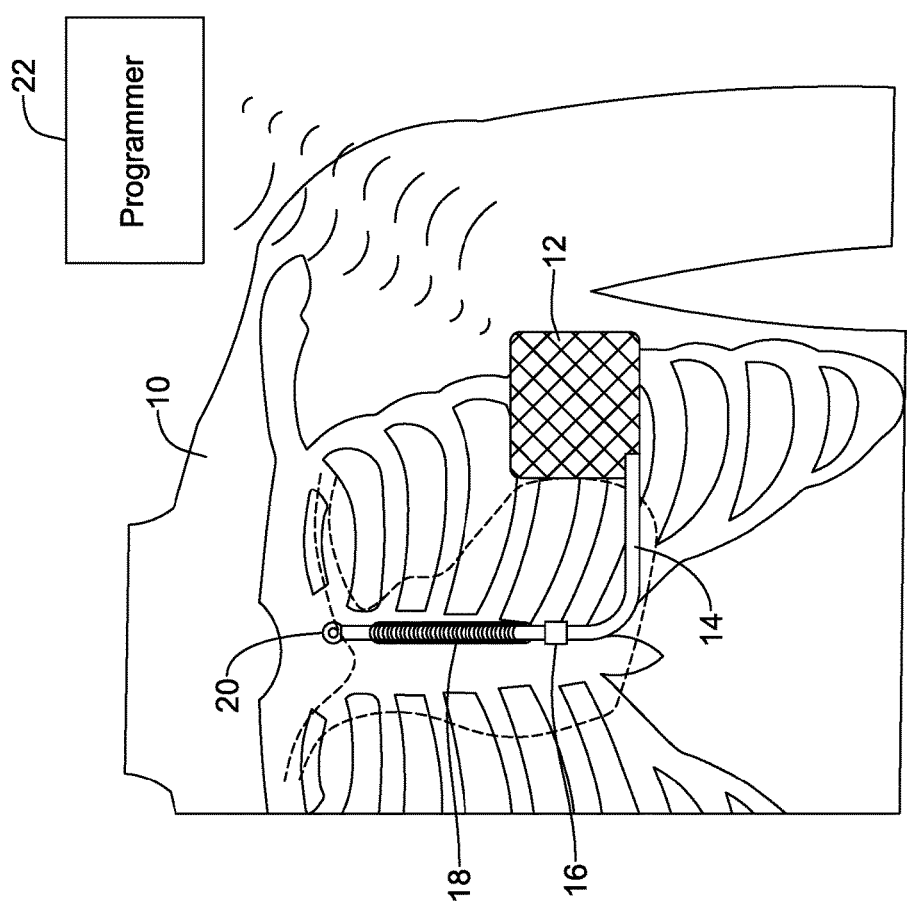
FIG. 1 shows an illustrative subcutaneous-only implantable cardiac stimulus system in an implanted state.

As explained above, FIG. 1 shows an illustrative subcutaneous-only implantable cardiac stimulus system in an implanted state. FIG. 2 illustrates certain aspects of the procedure to implant a device as in FIG. 1. In this illustration, the procedure for implantation calls for the use of three incisions at locations 30, 32 and 34. To reduce the risk of infection, a sterile field including approximately area 36 may be prepared. This largely tracks the method of implant described in the labeling approved in the United States for the S-ICD® System from Cameron Health and Boston Scientific at the time of approval by the FDA in 2012.

However, in many patients, this sterile field 36 will include various skin folds, for example with obese patients and/or due to proximity to the left breast. It is not always easy to get this area 36 clean for surgery, let alone keeping it clean and dry during the days or weeks after surgery while the incisions 30, 32, 34 all heal. For some patients, the incisions along the sternum may also present aesthetic concerns, for example, because incision 34 may leave a scar that can be visible when wearing ordinary and common clothing and incision 32 may be clearly visible when wearing swimwear.

Reducing the number of incisions has been proposed. Some may use, for example, a two-incision technique similar to that described in some embodiments of U.S. Pat. No. 7,655,014, the disclosure of which is incorporated herein by reference. In this technique, after tunneling between incision 32 and incision 30 and pulling the lead therethrough, an introducer tool having a splittable sheath is advanced from incision 32 toward the manubrium along the sternum, without making incision 34 at all. Next, the introducer tool is removed, leaving the sheath behind, and the lead is introduced through the sheath. Finally the sheath is split and removed over the lead. This approach relies on a suture sleeve at the xiphoid incision to secure the lead in place and prevent migration thereof. It may be desirable to provide additional anchoring for the lead near its distal tip along the upper sternum.

Figure 2:
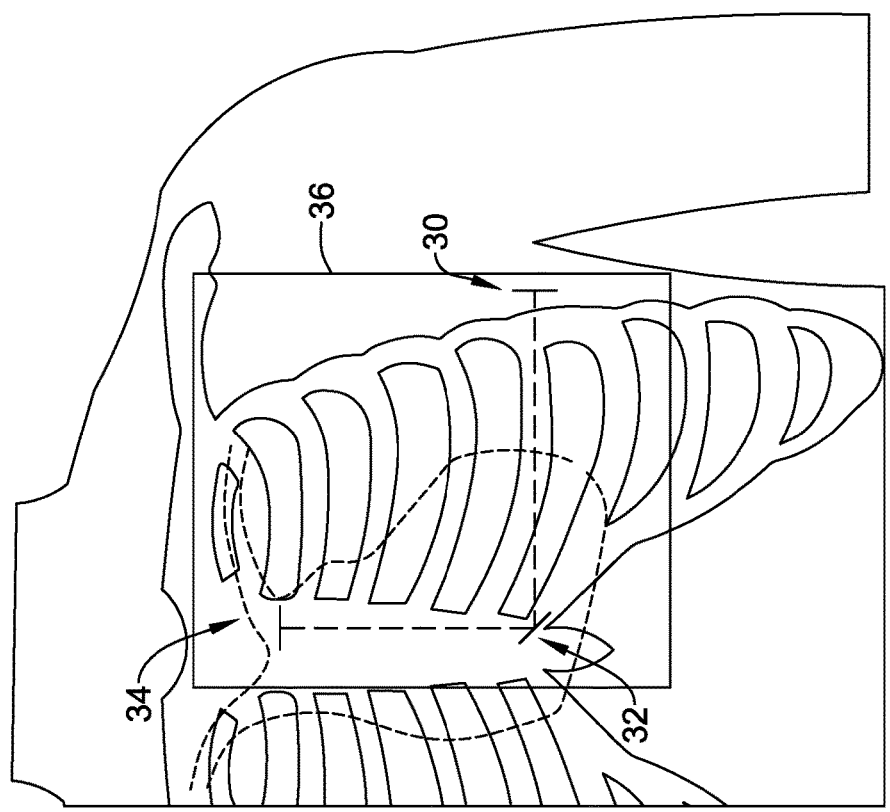
FIG. 2 illustrates certain aspects of the procedure to implant a device as in FIG. 1.
Figure 3:
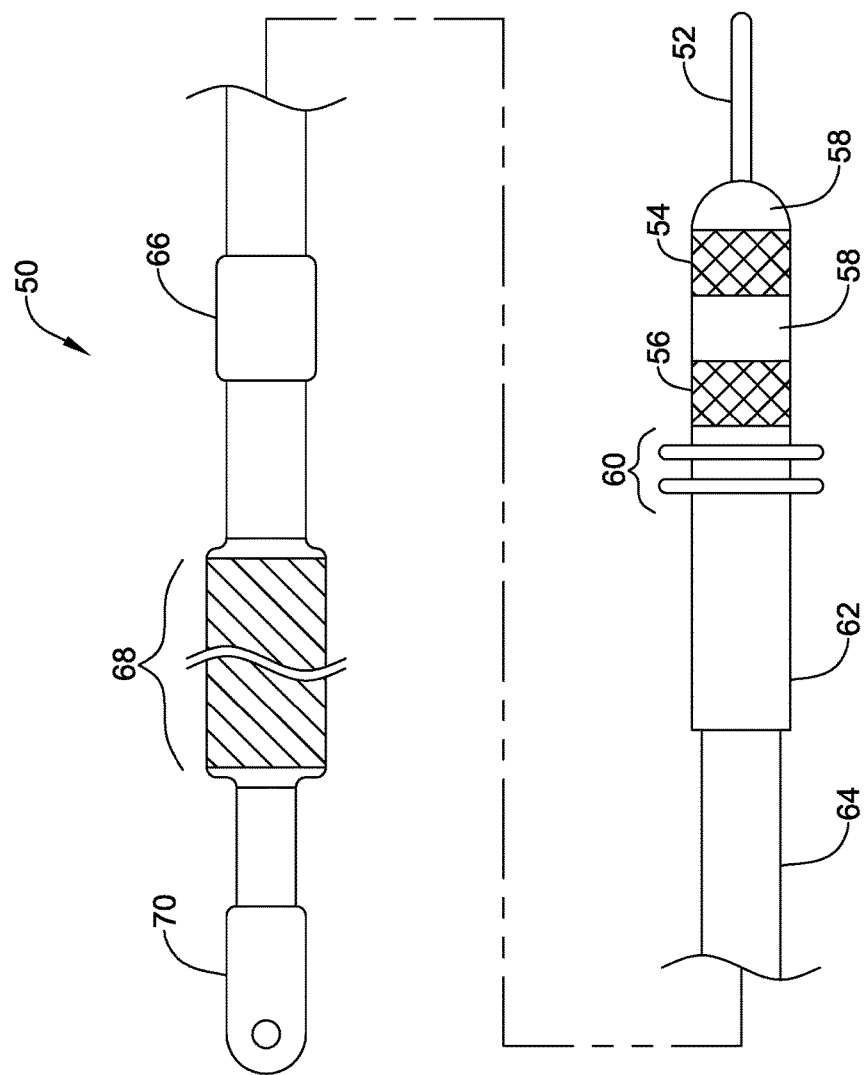
FIG. 3 shows an implantable lead similar to that of FIG. 1.

FIG. 3 shows an implantable lead similar to that of FIG. 1. The lead 50 has a proximal end with a proximal pin 52 which serves in this example as an electrical contact, along with additional contacts 54, 56, which are separated by insulating material 58. Seal plugs are shown at 60. A proximal plug sheath 62 is provided for a region near the proximal end of the lead 50. The pin 52, contacts 54, 56, insulating material 58 and seal plugs 60 are configured for placement inside a bore on a header of an implantable pulse generator. The lead 50 extends from this proximal configuration through an intermediate region 64 to a distal end having a proximal electrode 66, a coil electrode 68, and a distal tip electrode 70. Some illustrative discussion of a lead as used in the S-ICD™ System is provided in U.S. Pat. No. 8,483,841.

Lead 50 is shown for illustrative purposes, however, other designs and configurations including fewer, more or different electrodes 66, 68, 70, or contacts 52, 54, 56, may be used. Additional design elements such as bifurcation or other splitting, paddles or other designs may be used instead with an anchoring device attached at the time of implant. The lead 50 is not shown as including a passageway for a stylet to use during introduction, however, a lumen for that purpose may be provided if desired.

In the illustrative example, the lead 50 has a body that contains passageways having connectors therein for coupling the proximal contacts 54, 56 to the coil 68 and proximal electrode 66. The proximal pin 52 in an example is connected to the distal tip 70 by a stainless steel wire on which the lead body is coextruded lending significant pull strength to the design; other designs may be used. The proximal coupling for this subcutaneous lead is designed to prevent misuse in the vasculature, where the added stiffness caused by the coextruded central connector could be a perforation hazard. For at least these reasons, the lead 50 shown in FIG. 3 may not be compatible with standard plug designs (DF-1, DF-4, etc.) in transvenous defibrillators.

Figure 4B:
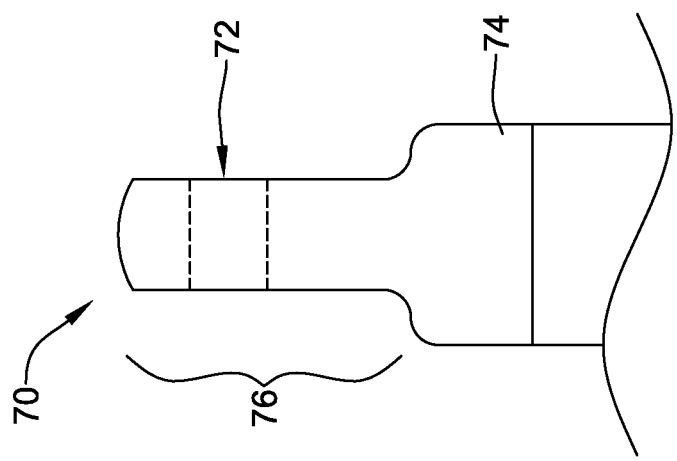
FIGS. 4A-4B are detail views of the distal tip of the lead of FIG. 3.
Figure 4A:
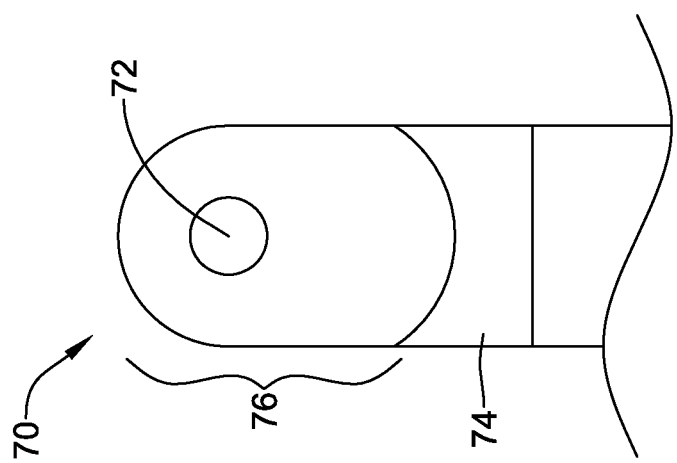

The distal tip electrode 70 is shown with an opening, such as a suture hole, details of which are shown in FIGS. 4A-4B. FIG. 4A shows that the tip electrode 70 has an opening, such as a suture hole 72, coupled to a base portion 74. The tip electrode 70 is thinned in region 76 as shown in the side view of FIG. 4B. Other designs may be used.

For a three-incision implantation as shown in FIG. 2, above, the suture hole 72 would be used to anchor the distal tip of the lead 50 to the tough connective tissue membrane that covers the sternum/ribs (the fascia). Such suturing would be performed using access via the upper sternal incision 34 (FIG. 2). However, if the upper sternal incision 34 (FIG. 2) is eliminated, anchoring by suturing to the fascia would not be possible at the distal tip, so an alternative design is desired that would allow a physician the flexibility to perform a three incision technique as shown in FIG. 2, or a two incision technique omitting the upper sternal incision 34 while using a distal anchor, with the same lead.

While the various examples herein are described in the contact of an implantable subcutaneous-only defibrillator, other devices/systems may make use of these designs and concepts for anchoring a lead or other device, for example, in an implantable monitor, an implantable neurostimulator, a transvenous pacemaker or defibrillator (or resynchronization system), a drug pump, or other devices.

Figure 5:
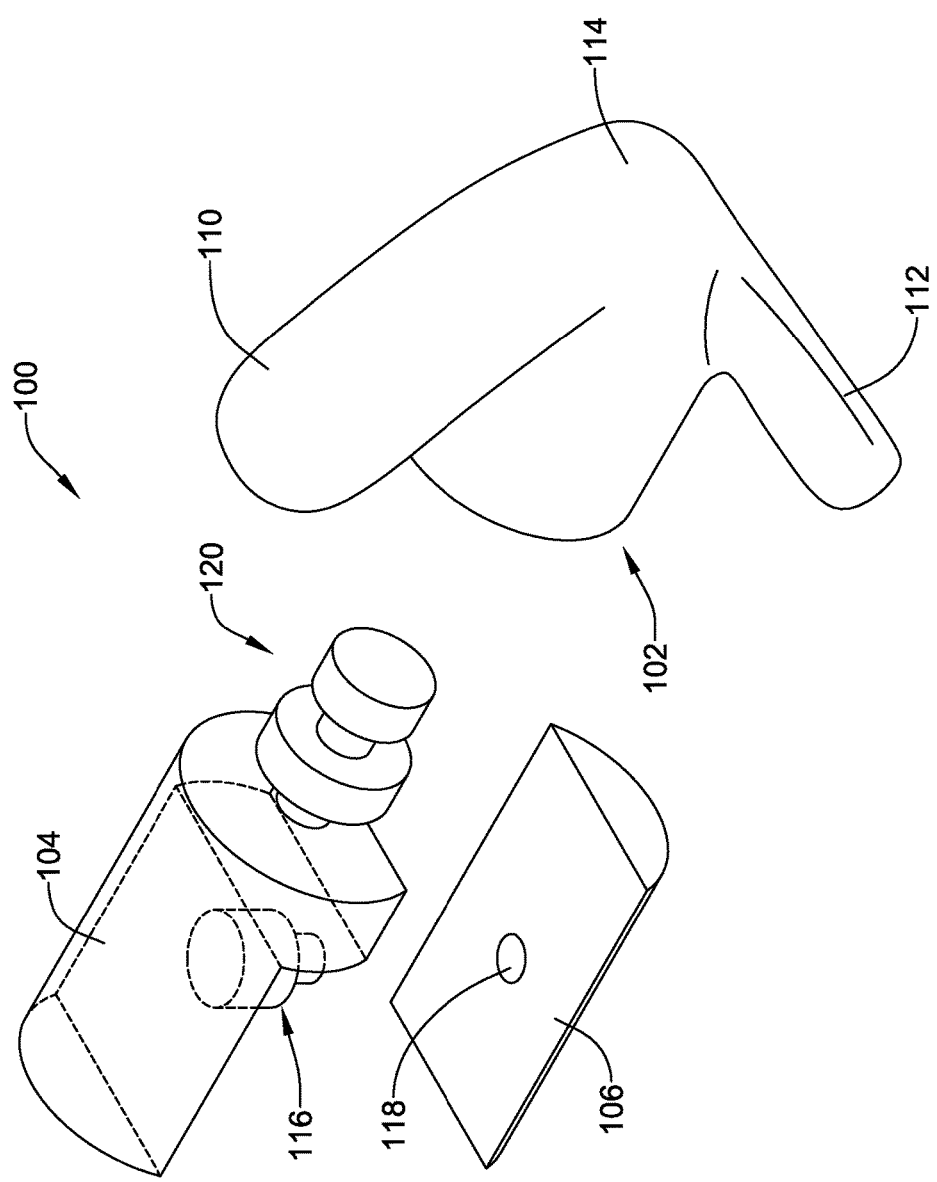
FIG. 5 is an exploded view of a first anchoring device.

FIG. 5 is an exploded view of a first anchoring device. The device 100 has three pieces: a body 102 with arms 110, 112 and a nose 114, an attachment feature 104, and a plate 106 designed to couple with the attachment feature 104. In an example, the body 102 is made of a relatively flexible material such as a silicone rubber, while the attachment feature 104 and plate 106 are made a harder material such as a polyether-ether-ketone (PEEK). Other materials may be used.

The attachment feature 104 includes a post 116 to which the plate 106 can attach with a corresponding hole 118. The post 116 extends in a lateral direction relative to the length of the device 100, which length is understood to run from the nose 114 to the opposing end of the attachment feature 104.

The post 116 may include a notch, indent, annulus, protrusion, or other element to create a snap fit relative to the plate 106. In an alternative embodiment, the plate 106 through-hole 118 may be threaded to allow a twist-on attachment. In yet another embodiment, the plate may include a male connector, rather than hole 118, for insertion into the post 116, which may be made hollow, or which could be replaced by an opening instead. Numerous other manners of connecting the plate 106 to the post 116 can be envisioned. A separate pin may be provided to use to secure the post 116 to the plate 108, for example.

In another example, all or parts of the attachment feature 104 and/or plate 106 may be conductive metal to facilitate cardiac or other signal sensing therethrough by an electrode to which the overall device 100 is attached. In yet another example, some or all of one or more of the body 102, attachment feature 104, or plate 106 may be porous or have small holes therethrough to allow sensing via tissue fluid passing therein to contact the underlying electrode of the lead to which the device 100 is attached.

The body 102, attachment feature 104, and/or plate 106 may have a coating of a radiopaque material such as titanium or a radiopaque paint/ink, or may integrate filaments, wires or the like having radiopaque properties. In an example, the body 102 is insert molded onto the attachment feature 104, using the alternating disks at 120 to ensure a secure connection. While not shown, the attachment feature 104 may also include screws, barbs, or hooks attached thereto to add to the connection strength relative to the body 102. In addition, surface texturing or the like may be provided on the body 102, attachment feature 104 or plate 106 to encourage tissue ingrowth once implanted.

The attachment feature 104 includes a post 116 to which the plate 106 can attach with a corresponding hole 118. The post 116 extends in a lateral direction relative to the length of the device 100, which length is understood to run from the nose 114 to the opposing end of the attachment feature 104.

The post 116 may include a notch, annulus, protrusion, or other element to create a snap fit relative to the plate 106. In an alternative embodiment, the plate 106 through-hole 118 may be threaded to allow a twist-on attachment. In yet another embodiment, the plate may include a male connector for insertion into the post 116, which may be made hollow. Numerous other manners of connecting the plate 106 to the post 116 can be envisioned. A separate pin may be provided to use to secure the post 116 to the plate 108, for example.

Figure 6:
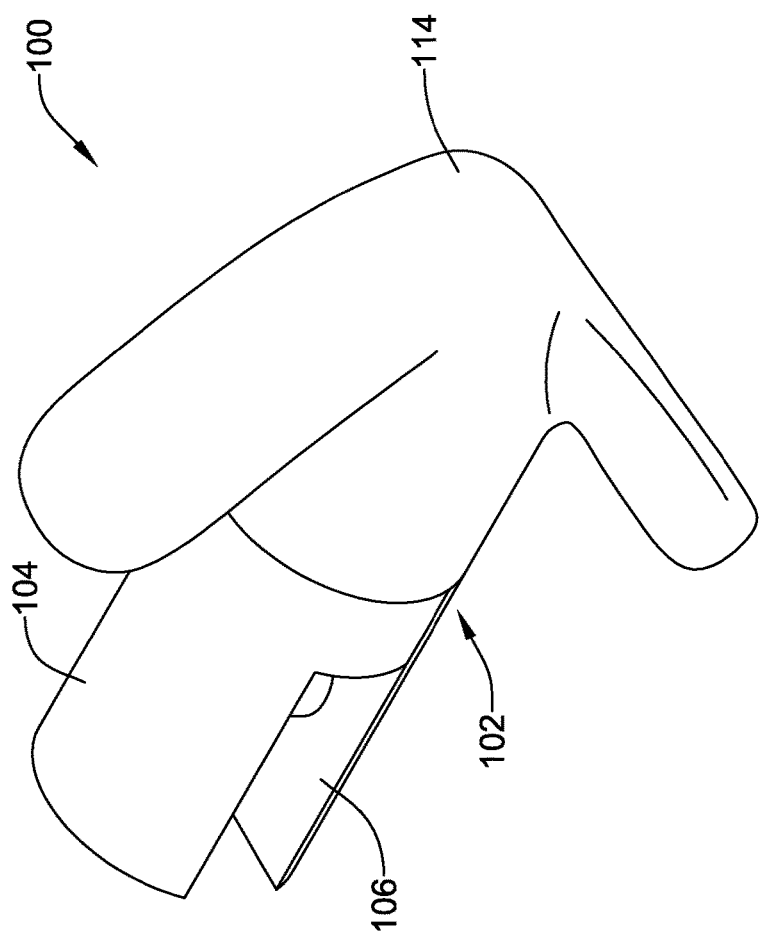
FIG. 6 is an assembled view of the first anchoring device of FIG. 5.

FIG. 6 is an assembled view of the first anchoring device 100 of FIG. 5. As noted, the body 102 can be insert molded onto the attachment feature 104. Alternatively, the body 102 may be snap fit and/or secured by an adhesive to, welded to, or heat shrunk over the attachment feature. In another example, the body 102, with arms 110, 112, and the attachment feature 106 are a single piece. As shown in FIG. 6, the plate 106 is attached to the attachment feature 104. The overall assembly provides a smooth outer profile for introduction into a patient.

Figure 7:
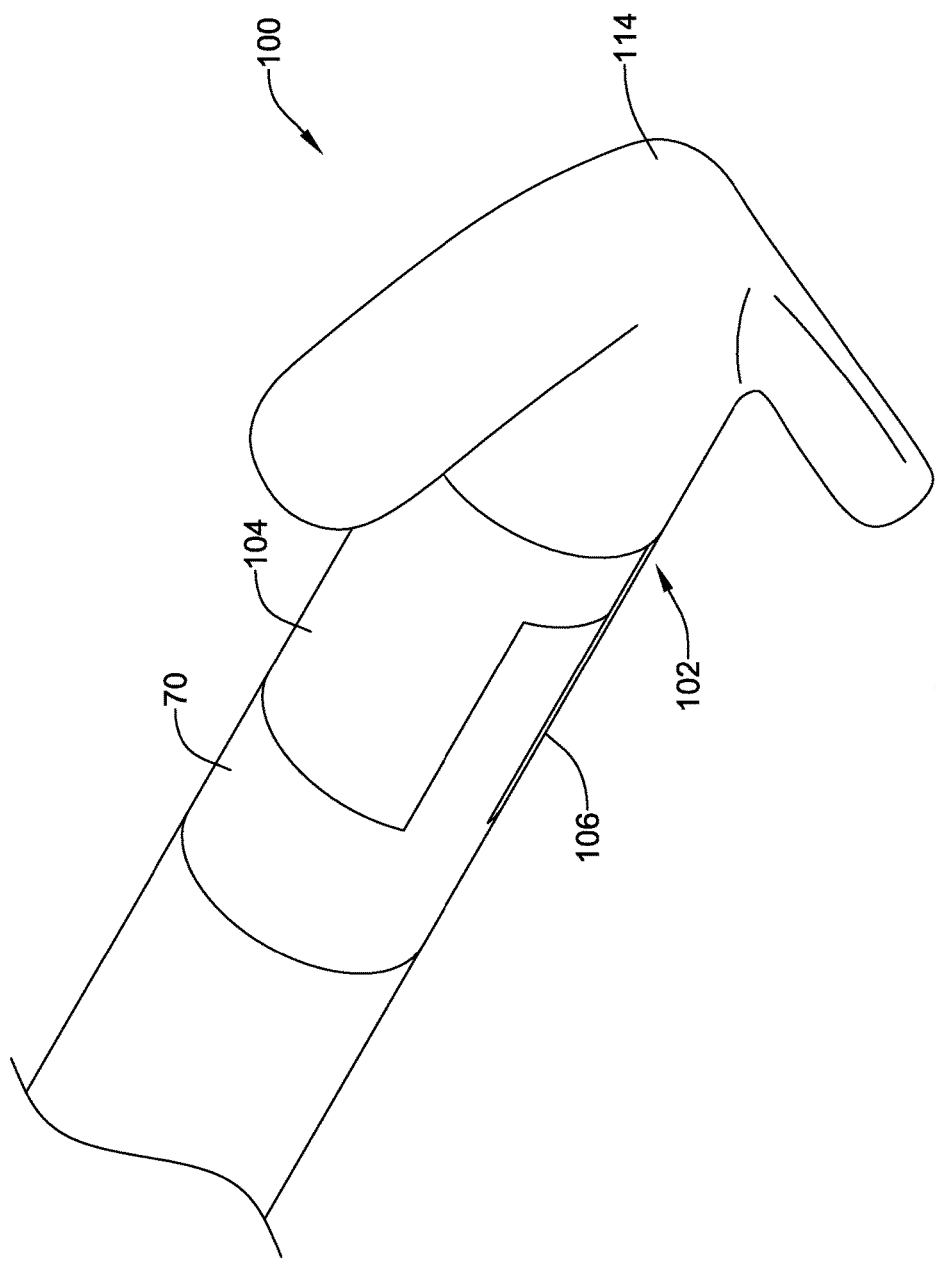
FIG. 7 shows the first anchoring device secured on the distal tip of a lead.

FIG. 7 shows the first anchoring device secured on the distal tip of a lead. The device 100 is attached, using the attachment feature 104, mated to the plate 106, to the distal tip electrode 70 of an implantable lead similar to that shown above in FIGS. 3, 4A and 4B. In particular, the attachment feature 104 and plate 106 take advantage of an opening, such as the suture hole in the electrode 70.

FIG. 8 shows a second anchoring device relative to the distal tip of a lead using a suture for attachment to the lead. The device is shown relative to a lead 200 having an opening, such as a suture hole 202, at a distal tip 204 thereof. The distal tip 204 may or may not be an electrode.

The anchoring device 210 includes arms or tines 212 in a generally t-shaped configuration. The tines 210 meet at body 214, which extends proximally from the tines 212 to define a bore having a closed end (at the tines). As with other figures, the location where the tines 210 meet may be described as a nose for the device 210.

Within the bore is an attachment feature that may take the form of a small loop or eyelet, to which a suture 220 is tied. The suture 220 may be permanently affixed to the body 214, rather than tied to a loop or eyelet. Rather than a suture 220, a metallic, polymeric or natural material (silk for example), or combination thereof, in the form of a monofilament, multifilament, braid, wound member, wire, staple, or clip, for example, or any suitable biocompatible filament having reasonable pull strength (for example, 1, 3, or 5 pounds, or more) may be used. Any of the embodiments above or below may use these other materials and/or structures instead of a suture. The suture 220 (or other attachment structure) is of a length that allows a gap between the anchoring device 210 and the distal tip 204 of the lead 200.

The tines 212 and rest of the body 214 may be molded as a single structure. Alternatively, the tines 212 and rest of the body 214 may overmolded onto a metal such as titanium to allow fluoroscopic observation of position. The tines 212 may be flexible to allow them to collapse during insertion in the patient for example as shown below in FIG. 10. The bore in the body 214 allows a distal portion of the lead 200 to be within the bore/body 214 during insertion without being permanently fixed therein.

During insertion, the lead would be pushed through a hollow sheath with the anchoring device 210 attached to the distal tip 204. As the lead 210 pushed through the sheath, the distal tip 204 would rest inside the bore defined by body 214 to improve pushability. Once a desired implant location is reached and the sheath is removed, the lead 200 and anchoring device 210 would become slightly separated, with the suture 220 securing the lead 200 to the anchoring device 210.

Figure 9B:
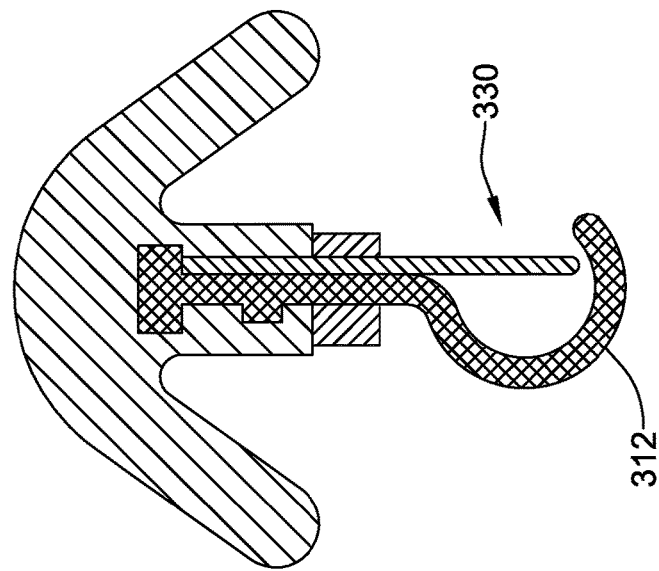
FIGS. 9A-9B show a third anchoring device.
Figure 9A:
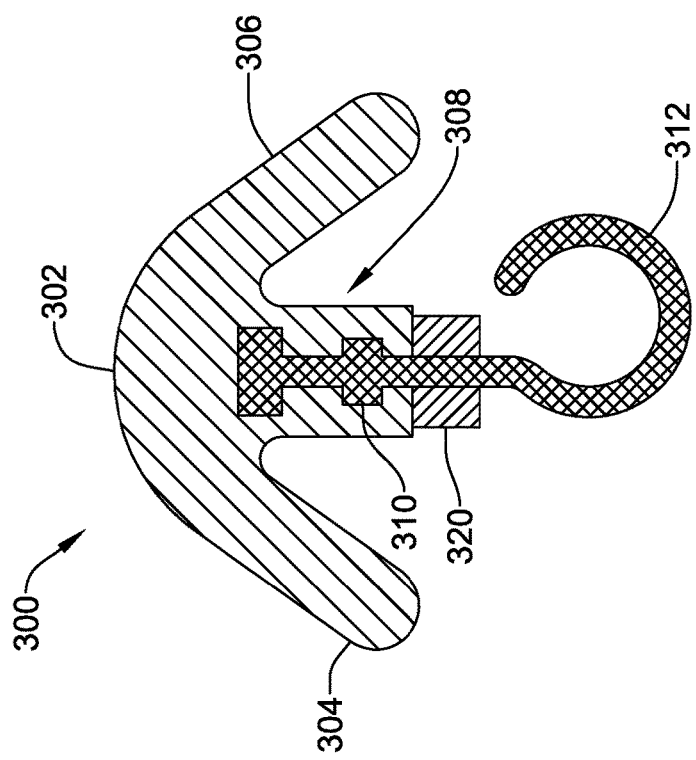

FIGS. 9A-9B show a third anchoring device. Referring to FIG. 9A, device 300 includes a nose at 302 and arms at 304, 306 as above with the first anchoring device. An attachment feature 310 includes a hook at 312. The attachment feature is shown embedded in the body 308 of the device 300.

The hook 312 may be extendable/retractable, with a spring structure, if desired, or may simply be in a fixed location. In this particular example, a dissolvable layer 320 is provided on the hook 312 for use during introduction so that a lead to which the hook 312 is attached is kept at a distance from the rest of the anchoring device 300. FIG. 9B shows an alternative in which a latch 330 is also provided to secure the distal end of a lead (not shown) to the hook 312. The latch 330 may be flexible in a first direction, inward into the space defined by the hook 312, to allow entry of the distal end of the lead (not shown) while relatively inflexible in the outward direction to prevent the lead from escaping.

Figure 10:
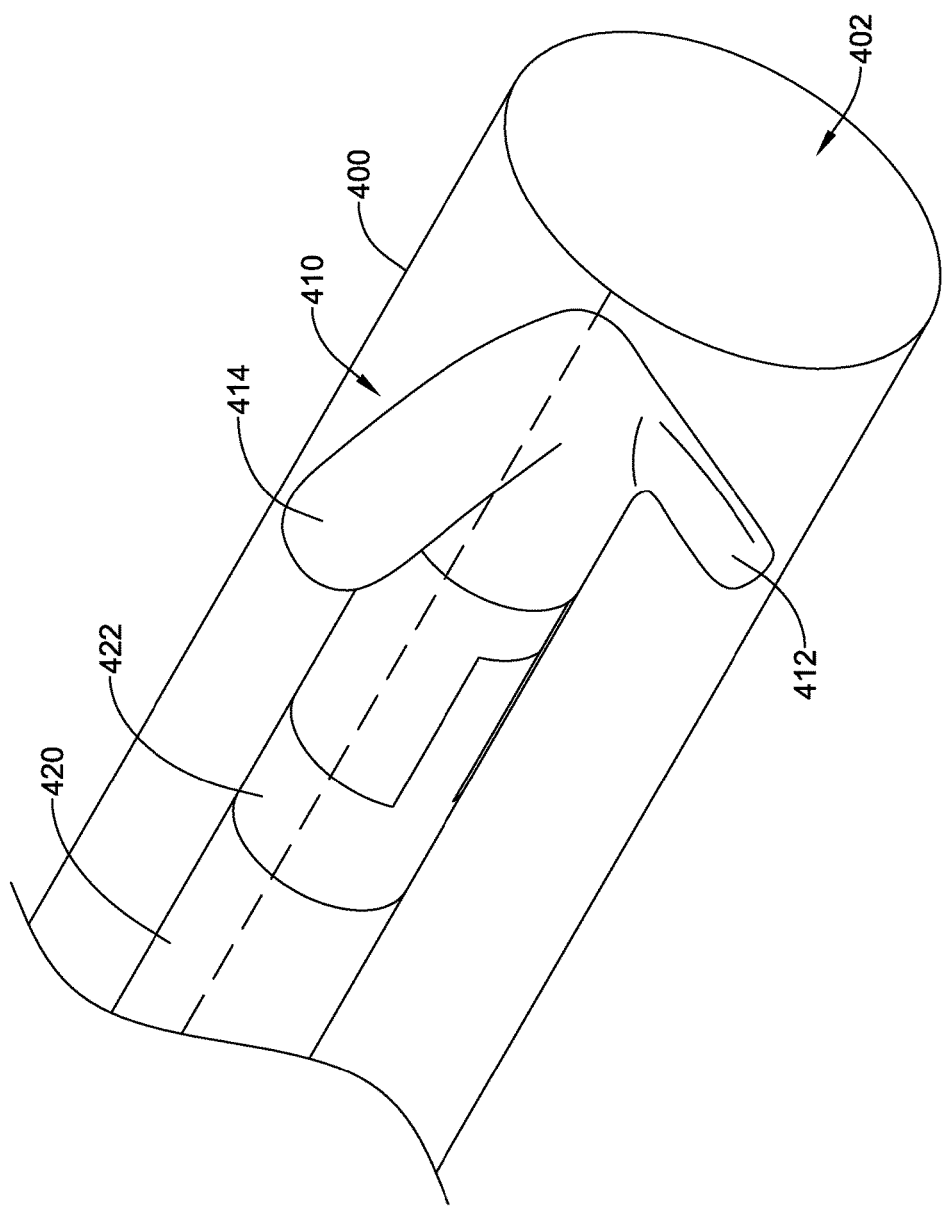
FIG. 10 shows insertion of a lead with an anchoring device thereon through a sheath.

FIG. 10 shows insertion of a lead with an anchoring device thereon through a sheath. The sheath is shown at 400 and may be, for example, a splittable sheath having a frangible, scored, or perforated line of weakness to allow it to be split along its length. The sheath 400 defines a lumen 402 in which an anchoring device 410 is shown with the arms 412, 414 in a collapsed state, compressed against the inner sides of the sheath 400. The anchoring device 410 is shown attached to a lead 420 at the distal tip 422 thereof. The distal tip 422 may be similar to those shown above, for example, in FIGS. 4A-4B. Once the anchoring device 410 exits the distal end of the sheath 402 and/or once the sheath 402 is removed by splitting it, the arms 412, 414 will extend out to a non-retracted, relaxed state, to create an anchor for the lead 420 at a desired position.

Figure 11B:
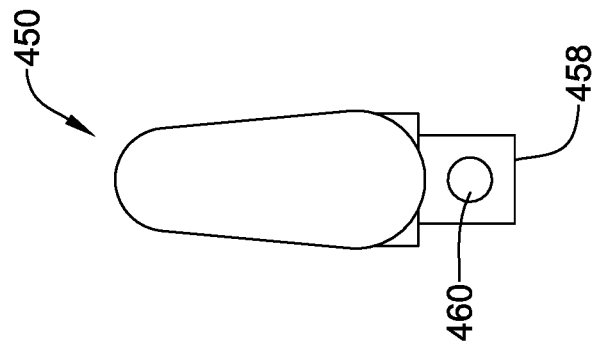
FIGS. 11A-11B show a fourth anchoring device.
Figure 11A:
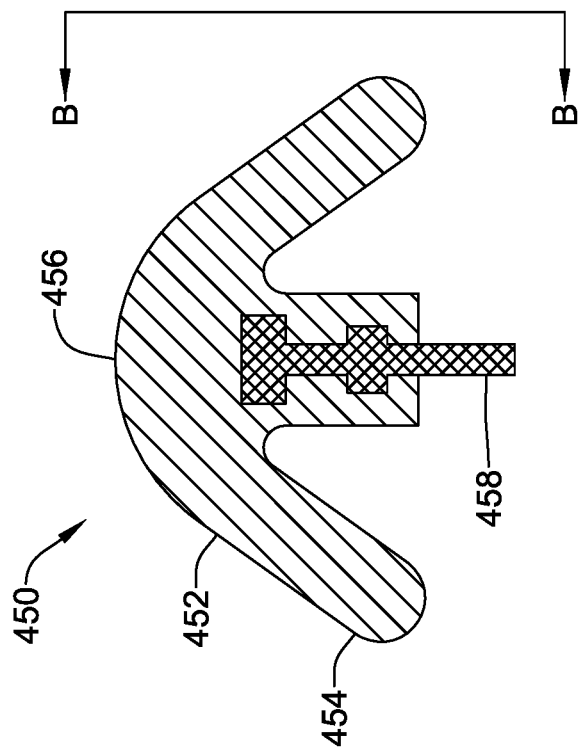

FIGS. 11A-11B show a fourth anchoring device. Referring to FIG. 11A, the anchoring device 450 includes a body 452 having a nose 456 and arms 454, with an attachment feature at 458 extending from the proximal end thereof. In this example, the attachment feature 458 is a tab having a hole 460 therethrough as shown in the side view of FIG. 11B. The hole 460 allows the anchoring device to be attached to the distal end of a lead using a suture, a surgical stable, or other connector. If desired, the body 452 of this embodiment may also extend in the proximal direction (where the nose 456 defines the distal end of the anchoring device 450) to define a bore for covering the distal end of the lead in a manner similar to that shown above in FIG. 8. The inclusion of such a bore may make introduction through a sheath as shown in FIG. 10 easier. The attachment feature 458 may be secured to the body 452 by overmolding or insert molding, adhesive, melt bonding, or welding, or the attachment feature 458 and body 452 may be formed as a single piece.

Figure 12:
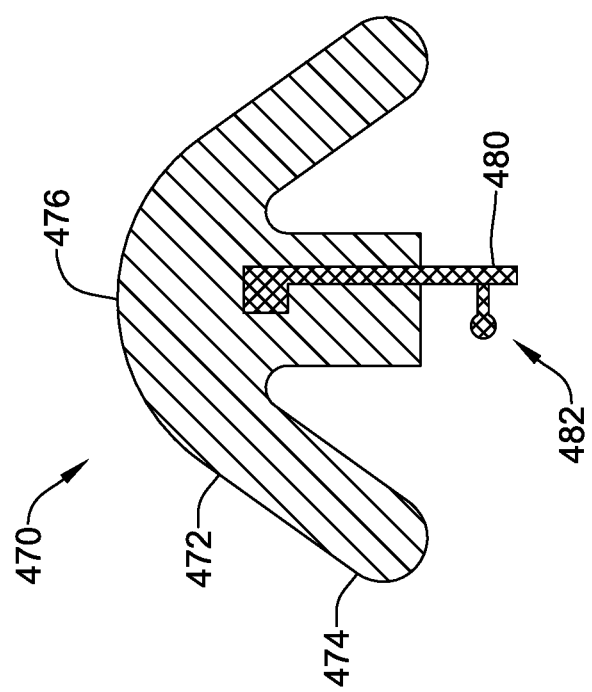
FIG. 12 shows a fifth anchoring device.

FIG. 12 shows a fifth anchoring device. In this instance, the anchoring device 470 includes a body 472 with arms 474 and a nose 476. An attachment feature 480 includes a post 482 extending in a lateral direction with an expanded head on the post, to allow placement through an opening, such as a suture hole of a lead such that the head keeps the post 482 secured to the lead. As before, the attachment feature 480 may be secured to, or formed as a single piece with the body 472.

Figure 13:
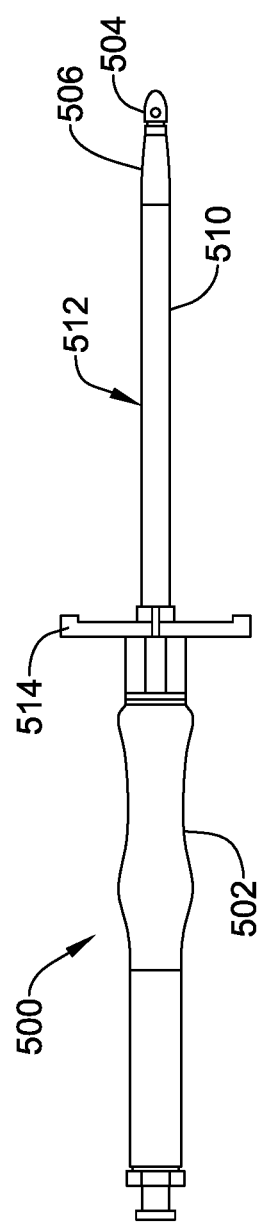
FIG. 13 shows a lead insertion tool having a sheath thereon.

FIG. 13 shows a lead insertion tool having a sheath thereon. The lead insertion tool 500 is sometimes also referred to as an electrode insertion tool or EIT. The tool 500 includes a handle at 502 and a distal tip at 504. The distal tip 504 may have a pointed but generally blunt end, to facilitate dissection of subcutaneous tissue, but is not sharp so as to avoid piercing through the skin inadvertently. Other designs may be used.

An opening, such as a suture hole may be provided on the tip 504, as shown. For example, the opening may be used to pull a lead during introduction from the lateral or axillary incision 30 (FIG. 2) to the xiphoid incision 32 (FIG. 2) by attaching a suture between the distal end of the electrode and the introducer tool.

It may be noted that the inclusion of a permanent anchor on the lead may not be a simple expedient. For example, since a pulling step is performed, such an anchor would need to have a design that allows the pulling step without harming the patient. Some concepts are shown in Published US Patent Application No. 20120029335, the disclosure of which is incorporated herein by reference.

Proximal of the distal tip 504 the lead insertion tool has a shaft 506 on which a splittable sheath 510 is disposed. The splittable sheath is shown with a longitudinal line of weakness at 512, allowing it to split in conventional fashion for splittable sheaths when the handles 514 are grasped and pulled apart.

In use, and referring again to FIG. 2 as well as FIG. 13, the insertion tool 500 may be inserted via the xiphoid incision 32 and advanced to the lateral incision 30, tunneling therebetween. The distal tip 504 exits the lateral incision 30 and is secured to the distal end of a lead (such as that shown in FIG. 3) with a suture. The tool is 500 is drawn out of the xiphoid incision, pulling the lead into the tunnel between the lateral incision 30 and the xiphoid incision. During each of these steps the splittable sheath 510 remains in place.

Next, the insertion tool 500 would be separated from the lead by snipping the suture tying the two together. The insertion tool 500 is again inserted through the xiphoid incision 32, this time going over the left margin (approximately) of the sternum, or 1-2 centimeters to the left thereof. Other directions and placements may be used, if desired. Once a desired position is achieved, the splittable sheath 510 is held in position while the insertion tool 500 is removed, leaving the splittable sheath in the now created second subcutaneous tunnel.

An anchoring device as in any of the above examples is then secured to the distal tip of the lead. The lead with the anchoring device thereon is then advanced through the splittable sheath 510 until a desired position is attained. While holding the lead in position, the splittable sheath is then split and removed. A suture sleeve may be placed over the lead at the xiphoid incision 32 and/or at the lateral or axillary incision 30. Finally, the proximal end of the lead would be inserted in the implantable pulse generator for the system, and the procedure would conclude typically with acute testing, sensing configuration, and other system checks and configuration steps, and closure of all the incisions 30, 32.

Figure 14:
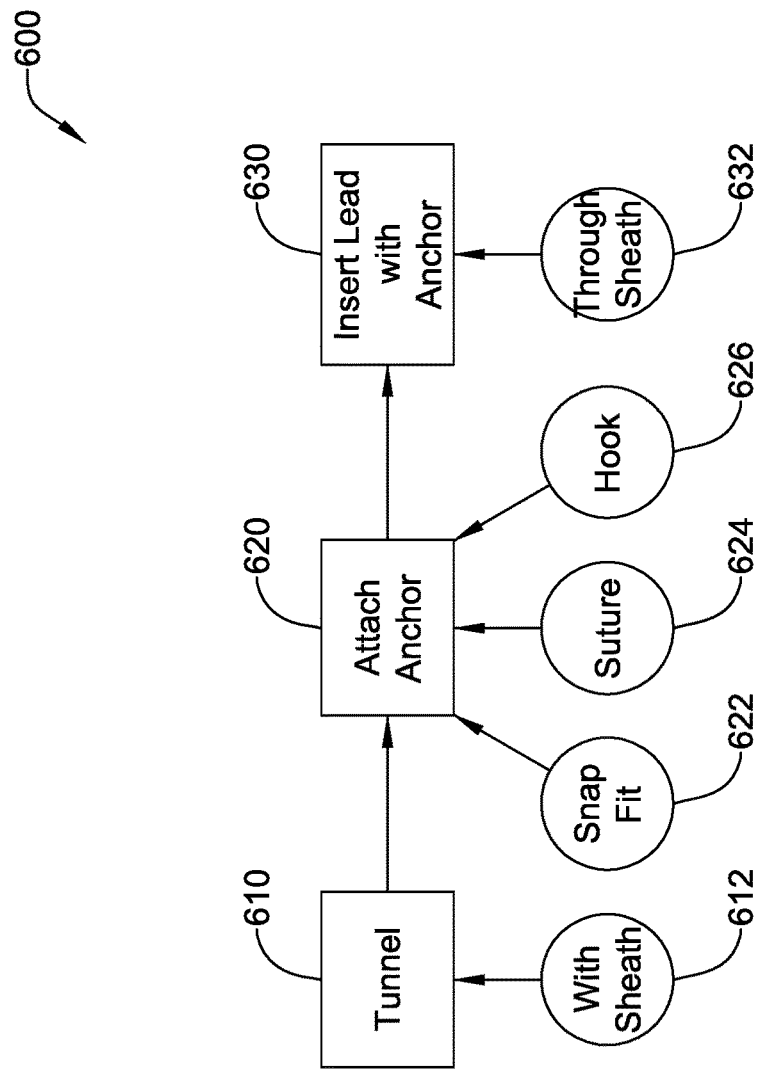
FIG. 14 is a block diagram for an illustrative method.

As relating more particularly to the lead introduction, FIG. 14 shows a method in block form. The method 600 includes forming a tunnel 610, attaching an anchor 620, and inserting the lead with the attached anchor 630.

In various examples, the step of forming a tunnel 610 may be performed with a sheath such as a splittable sheath being used, as noted at 612. The step of attaching an anchor 620 may be performed using a snap fit 622, a suture 624, a hook 626, or various other attachments discussed and shown above. The step of inserting the lead with the anchor 630 may be performed by advancing the lead and anchor through a splittable sheath as noted at 632.

In an alternative example, the sheath may be omitted at block 610, and the later step of inserting the lead and anchor 630 may be performed without the sheath in place, instead simply passing through the tunnel.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of implanting a subcutaneous lead having a plurality of electrodes thereon and a distal tip having an opening for use in attaching to another element, the method comprising:
   a physician securing an anchoring device to the distal tip using the opening prior to implanting the lead; and
   the physician advancing the lead, with the anchoring device secured thereto, through a first incision and a subcutaneous tunnel to a desired implant location;
   further comprising using an introducer tool having a sheath thereon for creating the subcutaneous tunnel and removing the introducer tool to leave the sheath in place,
   wherein the step of advancing the lead, with the anchoring device secured thereto, is performed by advancing the lead and anchoring device through the sheath.

2. The method of claim 1 wherein:
   the anchoring device comprises one or more arms thereon for anchoring in subcutaneous tissue;
   the one or more arms are flexible;
   the step of advancing the lead and anchoring device through the sheath is performed with the arms in a collapsed configuration; and
   upon completion of the step of advancing the lead and anchoring device through the sheath, the sheath is removed, allowing the arms to return from the collapsed configuration to an extended configuration for anchoring within the subcutaneous tissue.

3. The method of claim 1 wherein the anchoring device comprises:
one or more arms;
a body coupling the one or more arms together and having a nose on one end thereof; and
an attachment feature for attaching to a distal tip of the subcutaneous lead.

4. The method of claim 3 wherein the attachment feature of the anchoring device comprises a post extending in a lateral direction relative to a direction from the attachment feature to the nose, wherein the method comprises placing the post through the opening in the distal tip of the subcutaneous lead.

5. The method of claim 4 further comprising snap fitting a securing piece to the post to secure the post to the lead.

6. The method of claim 5 wherein the securing piece, attachment feature and body are configured to mate together with the distal tip of the subcutaneous lead to form a smooth transition therebetween.

7. The method of claim 4 wherein the post includes an expanded portion at a tip therefor, such that the method comprises passing the expanded portion of the post through the opening in the distal tip of the lead in a snap-through fashion and such that the anchoring device and the subcutaneous lead are secured together.

8. The method of claim 3 wherein the attachment feature comprises a hook, and the method comprises passing the hook through the opening in the distal tip of the subcutaneous lead.

9. The method of claim 8 wherein the attachment feature further includes a latch to allow entry of the subcutaneous lead opening to the hook, but preventing escape therefrom.

10. The method of claim 3 wherein the body comprises a bore having a closed end near the nose and an open end for receiving a portion of the distal tip of the subcutaneous lead, and the method comprises securing a suture to the body within the bore to secure the subcutaneous lead to the body.

11. The method of claim 10 wherein the step of securing the suture is performed to leave the suture long enough to allow the lead to be outside the bore while remaining attached to the suture.

12. The method of claim 3 wherein the attachment feature is a tab having an opening therethrough, and the method comprises securing an attachment member between the tab and the opening in the distal tip of the subcutaneous lead.

13. The method of claim 3 wherein the arms, body and attachment feature are formed of a single piece.

14. The method of claim 3 wherein the anchoring device includes a dissolvable portion that acts as a filler during introduction of the anchoring device and an associated subcutaneous lead into a patient, and then, once dissolved by tissue fluids after implantation, to create a space between the body and the anchored subcutaneous lead.

15. The method of claim 3 wherein the arms are flexible and configured to collapse for introduction through an introducer sheath, and the step of advancing the lead through a subcutaneous tunnel comprises inserting the introducer sheath into the subcutaneous tunnel and inserting the anchoring device and lead into the patient through the introducer sheath.

16. The method of claim 1 wherein prior to the physician securing the anchoring device to the distal tip, the method further comprises using the introducer tool to pull the lead from a second incision subcutaneously to the first incision where the distal tip exits the first incision, and the physician then securing the anchoring device to the distal tip.

17. A method of implanting a subcutaneous lead having a plurality of electrodes thereon and a distal tip having an opening for use in attaching to another element, the method comprising:
a physician securing an anchoring device to the distal tip using the opening prior to implanting the lead; and
the physician advancing the lead, with the anchoring device secured thereto, through a first incision and a subcutaneous tunnel to a desired implant location;
wherein prior to the physician securing the anchoring device to the distal tip, an introducer tool is secured to the opening in the distal tip of the lead and used to pull the lead subcutaneously from a second incision to the first incision, and
the method further comprises releasing the introducer tool from the opening in the distal tip before the physician securing the anchoring device to the distal tip using the opening.

18. The method of claim 17, wherein after releasing the introducer tool from the opening in the distal tip, the method further comprises inserting the introducer tool into the first incision and creating the subcutaneous tunnel to the desired implant location.

19. The method of claim 17 wherein the introducer tool is secured to the opening in the distal tip with a suture.

* * * * *